United States Patent [19]

Taniguchi et al.

[11] Patent Number: 4,839,017
[45] Date of Patent: Jun. 13, 1989

[54] POTENTIAL-CAUSING MEMBRANE FOR IMMUNOSENSOR

[75] Inventors: Isao Taniguchi; Kazuo Yasukouchi; Ichiroh Tsuji; Takeshi Fujiyasu, all of Kumamoto, Japan

[73] Assignee: Juridical Foundation the Chemo-Sero-Therapeutic Research Institute, Kumamoto, Japan

[21] Appl. No.: 31,264

[22] Filed: Mar. 30, 1987

[30] Foreign Application Priority Data

Mar. 31, 1986 [JP] Japan ................................. 61-74726

[51] Int. Cl.$^4$ ............................................ G01N 27/26
[52] U.S. Cl. ................................... 204/403; 435/291; 435/817
[58] Field of Search ...................... 204/403, 72, 59 R; 435/7, 291, 817

[56] References Cited

U.S. PATENT DOCUMENTS

| 3,574,072 | 4/1971 | Louvar | 204/72 |
| 4,081,334 | 3/1978 | Suzuki et al. | 204/403 |
| 4,352,884 | 10/1982 | Nakashima et al. | 204/403 |
| 4,363,634 | 12/1982 | Schall | 204/403 |
| 4,402,819 | 9/1983 | Rechnitz et al. | 204/403 |
| 4,444,878 | 4/1984 | Paulus | 204/403 |
| 4,444,892 | 4/1984 | Malmros | 436/528 |

Primary Examiner—John F. Niebling
Assistant Examiner—Steven P. Marquis
Attorney, Agent, or Firm—Fleit, Jacobson, Cohn & Price

[57] ABSTRACT

The present invention relates to a potential-causing membrane for use in immunosensors, which comprises an electrically-conductive film being prepared by electrolytic polymerization of an electrolytic polymerizable monomer, having at least one functional group, such as $NH_2$ group and COOH group, capable of binding an antigen or an antibody, and binding an antigen or an antibody through the functional group onto the film. Examples of the monomer include 3-bromopyrrole, 3,4-dichlorothiophene, 3-bromofuran, 0-chlorophenol and m-bromo-aniline.

2 Claims, 5 Drawing Sheets

POTENTIAL-CAUSING MEMBRANE FOR IMMUNOSENSOR

CROSS-REFERENCE OF THE RELATED APPLICATION

This application is related to the application Ser. No. 831,492 filed on Feb. 21, 1986 and assigned to the same assignee of this application.

BACKGROUND OF THE INVENTION (1) Field of the Invention

The present invntion relates to a potential-causing membrane for use as an immunosensor, i.e., a receptor which can identify an antigen or an antibody to be determined on the surface thereof and which can directly detect an immuno reaction occurring on the surface as an electrical current or voltage.

(2) Prior Art

In the field of clinical medical science, recently use of an immuno reaction, i.e., an antigen-antibody reaction, has come into general use to diagnose, prevent or cure diseases. Regarding clinic test methods, there have also been established various methods such as use of precipitation-agglutination reaction, fluorescent antibody technique, radioimmunoassay, enzyme-immunoassay and the like. However, since these conventional methods have some disadvantages such as that they require expensive equipment and sophisticated techniques to carry out the tests, such methods are very difficult to carry out on an everyday basis for qualitatively or quantitatively detection of biological substances, for example, in the home.

Nowadays, there are proposed new methods of detecting biological substances, which utilize antigen-antibody reaction carried out on the surface of a thin membrane, or on the interface of some solids. For example, Giaever et. al, found out that, when an antigen-antibody reaction is carried out on thin film comprising fine particles of indium coated on a glass plate, the degree of light transmission of the film greatly increases (J. Immunology, 110 (1973), 1424). Del Castillo et. al. reported that electrical resistance of lipid bimolecular membrane decreases when antigen-antibody reaction is carried out on the membrane (Science 153 (1966), 183). Suzuki, Aizawa, et. al. also reported fixing an antigen or an antibody is on a cellulose acetate membrane and determining the electrical potential of the membrane so as to detect biological materials (J. Membrance Sci., 2 (1977), 125 etc.). Furthermore, Janata showed that using concanavallin A as a substance similar to an immune fixed on a thin film formed of a polymer coated on the surface of a platinum electrode, it is possible to detect polysaccharides which specifically bond with concanavallin A by measuring the change in electric potential (J. Am. Chem. Soc., 97 (1935), 2914 ). Yamamoto, Tsubomura, et. al., proposed that it is possible to detect biological substances by measuring the change in electric potential between electrodes due to immune reaction, using electrodes comprising a chemically modified antigen or antibody (J. Chem. Soc. (1980), 1562). Thus, there have been proposed many immunosensors based on the clever utilization of both functions of identifying and binding antigen utilizing antibodies.

As described above, the immunosensor is based on the principle of immunoassay and is generally classified into marking immunoassay using a marker and non-marking immunoassay which does not use a marker. Regarding marking immunoassay, there has been invented a good determination device in which enzymes, metal chelate compounds, red blood cells, liposomes and the like are used as a marker and the respective final change is transformed into an electric signal by an electrochemical transducer. With the immunosensor, an extremely high sensitivity can be obtained by using chemical amplification.

On the other hand, with non-marking immunoassay, an antigen-antibody complex is formed on the surface of the receptor and the resulting physical change is directly transformed into an electric signal. So far there have been proposed two kinds of non-marking immunoassay, one being a membrane potential method in which a receptor is formed by binding an antibody (or antigen) onto the surface of the membrane and measuring the electric potential before and after the antigen-antibody reaction, and the other being an electrode potential method in which a receptor is formed by binding antibody (or antigen) directly or through membrane onto the surface of an electrode, and measuring the change in electrode potential caused by the antigen-antibody reaction. In this connection, the membrane or antibody bound (or fixed) on the surface of the electrode forms a stable complex by reacting with the antigen. The membrane or the antigen-antibody complex formed on the surface of the electrode induces a change in membrane potential or electrode potential.

An immunosensor which determines electrical potential based on the above-described principle is a new method that is recently attracting attention and which is being studied, since antigens and antibodies can be directly and easily detected according to the method. However, since the response time of a non-marking immunosensor of either of the above two kinds is long (not less than 30 minutes) and the electrical sensitivity of the response is also low, the properties of the non-marking immunosensor are not sufficient. It is therefore necessary to improve the properties of the immunosensor in practical use.

In the immunosensor as described above, there are some cases where a receptor of the electrode potential type is formed by binding antigen (or antibody) directly onto the surface of the electrode, but as a rule, a receptor, i.e., a potential-causing membrane of the above two types, is formed by chemically or physically fixing an antigen (or antibody) onto the surface of a membrane of a molecular compound such as cellulose acetate, sephadex, polystyrene, polyamide or the like. In this regard, it is estimated that electrical response of the membrane mainly depends on the amount of antigen (or antibody) which is fixed onto the membrane, an depends on the electrical conductivity of the membrane perse. The membrane perse generally has insulative properties.

SUMMARY OF THE INVENTION

The present inventors have already invented a potential-causing membrane for use in immunosensors, which comprises an electrically-conductive film of polypyrrol or polythioplene; good results have been thereby obtained (U.S. Ser. No. 831,492). The present invention is an improvement of the invention as described above.

It is, therefore, a primary object of the present invention to provide a novel potential-causing membrane for use in immunosensors, which can be prepared easily to obtain the desired immunoresponse characteristics.

The present inventors have found that this object can be accomplished by the use of an electrically-conductive film being prepared by electrolytic polymerization of electrolytic polymerizable monomer, having at least one functional group capable of binding an antigen or an antibody, and binding antigen or antibody through the functional group onto the membrane.

DESCRIPTION OF THE PREFERRED EMBODIMENTS

Figure 1:
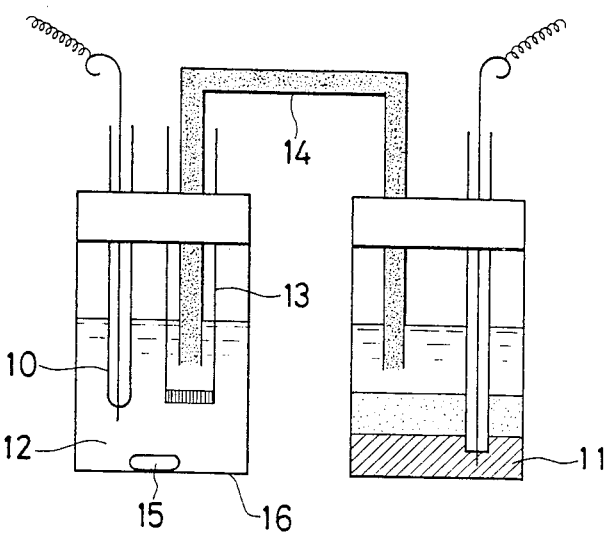
FIG. 1 shows an example of an immunosensor system including an antigen (or an antibody) fixing polymer coated electrode of the present invention as a working electrode.

The electrically-conductive polymer for use in preparation of the potential-causing membrane of the present invention can be prepared by means of electrolytic polymerization of electrolytic polymerizable monomer. The electrolytic polymerizable monomer is well-known, and examples of the monomer include pyrrole, thiophene, furan, phenol, aniline and the like.

Use of the above monomer to prepare the membrane of the immunosensor provides good advantages. That is, a uniform film can be directly formed on an electrode by electrolytic polymerization of the monomer, and therefore, the resulting electrode can be used as a working electrode for immunosensor without further processing of the electrode. It is also easy to form a film having the desired thickness by controlling the amount of current or current density during the polymerization.

As for introducing at least one functional group capable of binding an antigen or an antibody in the above-described polymer film materials, this can be effectively carried out by using a monomer having such a functional group. This can also be carried out by introducing functional groups in a film prepared by electrolytic polymerization of electrolytic polymerizable monomer. Examples of the functional group include a halogen (which can bind an antigen or an antibody with an amino group of protein, phenolic hydroxy group by acetylation), CHO group, COOH group and epoxy group (which can react with $NH_2$ group of an antigen or an antibody), and $NH_2$ group (which can react with COOH group of an antigen or an antibody). These functional groups should be in the position of the monomer other than the position where an electrolytic polymerization of the monomer is prevented. Examples of the monomer having the functional group include halogenated monomers such as 3-bromopyrrole, 3-chloropyrrole, 3-bromothiophene, 3,4-dibromothiophene, 3,4-dichlorothiophene, 3-bromofuran, 3-chlorofuran, 0-bromophenol, 0-chlorophenol, m-bromoaniline and the like; monomers having substituted COOH group or CHO group such as pyrrole-3-carboxylic acid, pyrrole-N-carboxylic acid, thiophene-3-carboxylic acid, m-oxybenzoic acid, thiophene-3-aldehyde and the like; and monomers having $NH_2$ group such as P-(2-aminoethyl) phenol (tyramine), N-(3-aminopropyl) pyrrole and the like. These monomers can be prepared by the conventional method, and can also be obtained as commercial products.

The electrolytic polymerization of the monomer having the functional group (hereinafter, referred to as said monomer) can be conducted by the conventional methods, e.g., electrolytic oxidative polymerization using constant electrical current or electrolytic oxidative polymerization using constant electric potential. That is, a working electrode for use in electrolytic polymerization and a counter electrode are placed in an electrolytic polymerization solution containing said monomer, and a polymer membrane is obtained by electrical conduction therethrough at a constant current or voltage under suitable conditions for the electrolytic polymerization.

In the first stage, said monomer is dissolved in a solvent for electrolytic polymerization so as to prepare an electrolytic polymerization solution. The solvent is a polar solvent which will dissolve said monomer but will not dissolve said polymer. Examples of such solvents include nitriles such as acetonitrile and benzonitriles; amides such as dimethyl formamide; amines such as pyridine; ethers such as tetrahydrofuran and 1,4-dioxane; acids such as acetic acid; alcohols such as methanol and ethanol. There may also be included such solvents as propylene carbonate, nitromethane, methylene chloride, acetone, methylethyl ketone, water and the like. Said monomer is dissolved in one or more of these solvents, in a concentration generally in the range of 20 to 200 m moles/l.

There can also be used solvents such as water having relatively small solubility, i.e, not more than 1 mol/l of monomer.

Furthermore, if desired, an appropriate monomer solution can be prepared by changing the condition of the solution, e.g., in line with the fact that a monomer having amino group can easily be dissolved in an acid solution and a monomer having carboxylic group can also easily be dissolved in an alkaline solution.

In forming the electrolytic polymerization solution, it is preferable, depending upon the type and the amount of solvents, to add an electrolytic substance such as tetraalkylammonium-boron-tetrafluoride, tetraalkylammonium perchlorate, tetraalkylammonium-phosphorus-hexafluoride or tetraalkyl hydrogensulfate, in which the alkyls have 1 to 10 carbon atoms. For example, when a nitrile such as acetonitrile is used as solvent, it is preferable to add an tetraalkylammonium-boron-tetrafluoride, tetraalkylammonium perchlorate or the like in an amount of 50 to 100 m moles/l. 1,4-Dioxane, propylene carbonate, acetone or nitromethane is used concurrently with the addition of tetrabutylammonium-boron-tetrafluoride or tetraethylammonium perchlorate in an amount of 50 to 100 m moles/l. When a relatively conductive solvent such as water is used, the addition of an ordinary inorganic salt, an acid, an alkali, a buffer solution or tetraethylammonium is preferred.

In the electrolytic polymerization solution thus prepared, there are placed a working electrode and a counter electrode, while a reference electrode (e.g. a saturated calomel electrode, Ag/AgCl electrode or $Ag/AgClO_4$ electrode) may also be concurrently used, and then electric current is passed between these electrodes under suitable current density and electric charge so as to start the electrolytic polymerization of monomers. It is preparable that such polymerization be conducted in a solution from which dissolved oxygen has been removed, and most preferable that it be conducted under an atmosphere of nitrogen. Immediately after the passage of electricity is started, the polymer film starts to be formed on the working electrode (electrode body). In this connection, the film thickness of the film formation rate is determined by electric charge and current density, depending upon the type of monomer and solvent used and other operating parameters. For example, in a case where pyrrole derivatives having a functional group are used and acetonitrile is used as solvent, a polymer film of a thickness of about 50 to 1000 nm, preferably about 100 to 250 nm is produced by an electric charge of 20 to 100 mC/cm$^2$ at a current density of 20 to 5000 µA/cm$^2$, while the use of an aqueous solvent for producing a polymer film of the same thickness requires about ten times as much current density and about 5 to 20 times as much electric charge. Therefore, the current density and the electric charge should be determined based on the kinds of the solvents used, the condition of the process and the thickness of the film to be formed. As materials for the working electrode, there can be used those which can ordinarily be used for a working electrode in a biosensor. Examples of the materials include metals such as platinum, aluminum and gold; metal oxides such as tin oxide and titanium oxide; semiconductive substances such as silicone and gallium arsenide; and carbonaceous substances such as graphite and glassy carbon. These electrodes can be used in any shape known in the art.

The electrode body (working electrode) on which a polymer film has been formed in the manner as described above is subjected to a washing operation and then immersed in a solution containing an antigen or an antibody for binding or fixing the antigen or the antibody thereon. Alternatively, the polymer film is separated or exfoliated from an electrode body, washed and then immersed in an antigen- or antibody-containing solution.

A preferred solution containing an antigen or an antibody is, for example, one which has been adjusted to pH 7.0 with a phosphate buffer. The operation of immersing the polymer film-formed electrode or the polymer film in the antigen- or antibody-containing solution must be carefully conducted so that the antigen or the antibody is bound or fixed onto every functional group of the film in a highly dense and homogeneous state in order to prevent the adsorption of any non-specific substance, i.e. reactions other than the desired antigen-antibody reaction which is to be detected by the immunosensor. The prevention of such non-specific adsorption may be enhanced by the treatment of the antigen- or antibody-fixed electrode or film (membrane) with a suitable agent such as BSA (bovine serum albumin), or monoethanolamine.

If necessary, the polymer film on which an antigen or an antibody is fixed or bound can be treated with sodium hydrogen borate or the like so as to stabilize the fixation between the polymer and the antigen (or the antibody) and also improve the degree of freedom of the fixed antigen or antibody.

It is also preferable that the electroconductivity of the polymer film used in the present invention be $10^{-4} \Omega^{-1}$ cm$^2$. This is because it requires a long time to form the polymer film by the electrolytic polymerization and to detect an antigen or an antibody when the electroconductivity of the film is not more than $10^{-4} \Omega^{-1}$ cm$^2$. In addition, at less than this value the S/N ratio becomes low in case of using an inexpensive voltmeter (input resistance of more than about 10 MΩ.

Any type of antigen or antibody can be bound or fixed onto the functional groups of the polymer film according to the present invention. Such antigens (or antibodies) include various immunoglobulins (IgG, IgM, IgA, etc.) anti-immunoglobulins, albumines, and hCG.

The fixation or binding of an antigen or an antibody onto the functional polymer film can be carried out concurrently with the polymerization by adding in advance the antigen or the antibody into the solution for electrolytic polymerization where an aqueous solvent is used. This procedure is advantageous in that the polymer film on which an antigen or an antibody is fixed can be produced in a single step.

The antigen (or antibody) fixed film prepared in the above-mentioned manner can be used as a potential-causing element for an immunosensor, in the form of an electrode (shown in FIG. 1) in which an electrode body is coated with the antigen (or antibody) fixed-film, or in the form of a membrane (shown in FIG. 2) in which the antigen (or antibody) fixed-film is used by itself. The thickness of the potential-causing membrane is preferably between about 0.5µ and about 5µ, i.e. about 10 to 20 times as large as that of the electrode (between about 0.05µ and about 0.25µ), since it is difficult to exfoliate an extremely thin film from the electrode body.

FIG. 1 illustrates a typical example of immunosensor system including an electrode 10 according to the present invention, which comprises an antigen (or an antibody) -bound electrically-conductive film overcoating an electrode body, and a reference electrode 11. The reference electrode 11 is any suitable electrode used in the art, such as a saturated calomel electrode or an Ag/AgCl electrode. The working electrode 10 is immersed in an antibody (or an antigen)-containing solution 12 in a container 16. The solution 12 is connected with the electrode liquid of the reference electrode through a connecting tube (or bridge) 14 having a filter 13. Thus, the electric potential (more specifically, the change in the potential) caused across the working electrode 10 due to antigen-antibody reaction is detected by a voltmeter (not shown), while the solution 12 is preferably stirred with a stirring device such as a magnetic stirrer 15.

Figure 2:
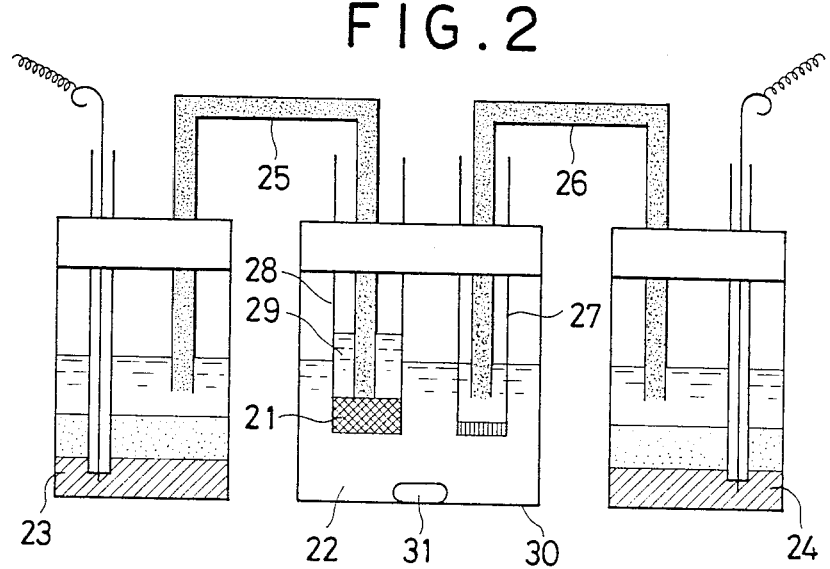
FIG. 2 shows an immunosensor system using an antigen (or an antibody) fixing polymer film of the present invention as a potential-causing membrane.

FIG. 2 illustrates an example of an immunosensor system where an antigen (or an antibody) -bound electroconductive film is used as it is, i.e. in the form of a membrane, for measuring the membrane potential (more specifically, the change in membrane potential) due to the antigen-antibody reaction. Thus, the system of FIG. 2 includes the antigen (or the antibody) -bound membrane 21 provided between two saturated calomel electrodes 23, 24 as reference electrodes. The membrane 21 is mounted on a glass tube 28 containing a dilution liquid (a saline solution or PBS) 29, the concentration of which is about one tenth of that of a saline solution or PBS used to prepare a solution containing an antibody (or an antigen) to be detected. The electrode 23 is connected with the liquid 29 through a bridge 25 while the electrode 24 is connected with the solution 22 in a container 30 through a bridge 26. The measurement of a membrane potential across the membrane 21, preferably while stirring the solution 22 with a magnetic stirrer 31, with such system enables detection of the objective antibody (or the antigen) in the solution. The wheresaid detecting system can be made smaller, e.g., by limiting the amount of the solution to be detected to about 0.1 ml, the only condition being that the above basic elements must be provided.

A potential-causing membrane according to the present invention can be used as a sensor for a marking immune system using a marker such as a radioisotope, enzyme or fluorescent material. Such a marking immune system is useful for microanalysis.

The present invention will be explained with reference to the following non-limitative examples.

EXAMPLE 1

In each of the solutions shown in Table 1 was immersed a working electrode made of platinum wire (1 mm in diameter and 5 mm in length) and a counter electrode made of platinum plate, and electrolytic polymerization was conducted under the condition specified in Table 1 to obtain an Pt electrode overcoated with the polymer. The so-obtained electrode was washed with the solvent used in the polymerization, washed with water, and then immersed in IgG solution having a concentration of 150 mg/l for one day, and was further immersed for one night in a phosphate buffering solution containing 0.05M ethanolamine (pH 6.82) so as to obtain an IgG fixed-polymer coated Pt electrode.

Figure 3:
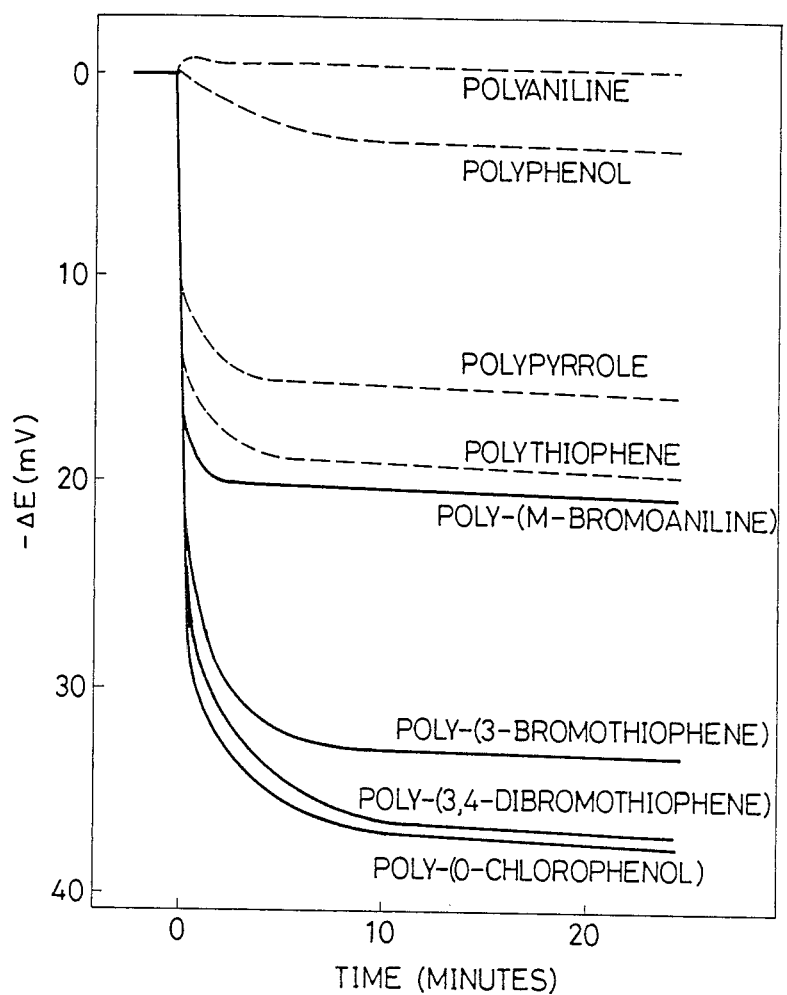
FIG. 3 is a graph showing the responses of antigen (IgG) fixed polymer films of the present invention.

The change in electrode potential ($-\Delta E/mV$) was measured before and after the fixation of the anti-IgG. The results are shown in FIG. 3. As is obvious from FIG. 3, each electrode overcoated with an electroconductive polymer having a functional group of the present invention exhibited a good response.

TABLE 1

| No. | Monomer | Solvent & monomer concentration | Electrolyte | Electric density (mA/cm$^2$) | Electric charge (mc/cm$^2$) | Electrolytic method | Polymer structure | Thickness of formed film (nm) |
|---|---|---|---|---|---|---|---|---|
| *Present invention* | | | | | | | | |
| 1 | 3-bromothiophene | acetonitrile, 0.1M | 0.1M [CH$_3$(CH$_2$)$_3$]$_4$N.BF$_4$ | 12.5 | 375 | Constant current | (thiophene with Br) | 500 |
| 2 | 3,4-dibromothiophene | acetonitrile, 0.1M | 0.1M [CH$_3$(CH$_2$)$_3$]$_4$N.BF$_4$ | 18.6 | 3730 | Constant current | (thiophene with Br, Br) | 250 |
| 3 | O—chlorophenol | H$_2$O, 0.1M | 0.1M NaOH | 3.0 | 3730 | Constant current | (phenol with Cl) | 200 |
| 4 | m-bromoaniline | H$_2$O, 10 mM | 0.1M KCl | +1.5 V vs SCE | 75 | Constant potential | (aniline with Br) | 200 |
| *Comparative examples* | | | | | | | | |
| 5 | Pyrrole | Acetonitrile, 0.1M | 0.1M [CH$_3$(CH$_2$)$_3$]$_4$N.BF$_4$ | 0.1 (100 μA/cm$^2$) | 80 | Constant current | (pyrrole) | 200 |
| 6 | Thiophene | Acetonitrile, 0.1M | 0.1M [CH$_3$(CH$_2$)$_3$]$_4$N.BF$_4$ | 12.5 | 373 | Constant current | (thiophene) | 500–900 |
| 7 | Phenol | H$_2$O, 0.1M | 0.1M, NaOH | 1.25 | 3730 | Constant current | (phenol) | 500–1000 |

TABLE 1-continued

| No. | Monomer | Solvent & monomer concentration | Electrolyte | Electrolytic condition Electric density (mA/cm²) | Electric charge (mc/cm²) | Electrolytic method | Polymer structure | Thickness of formed film (nm) |
|---|---|---|---|---|---|---|---|---|
| 8 | Aniline | H₂O, 0.1M | 0.1M, H₂SO₄ | +0.8 V vs SCE | 125 | Constant potential |  | 200 |

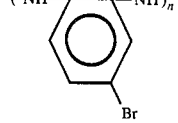 or  can be included in Nos. 4 and 8.

EXAMPLE 2

An electrolytic polymerization of tyramine (p-(2-aminoethyl)-phenol.

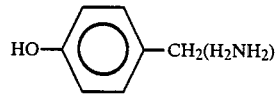

conducted by constant voltage-electrolytic polymerization under the following conditions:

| | |
|---|---|
| Working electrode | 1 mmφ, 5 mm length |
| Counter electrode | Pt plate |
| Solvent | Methanol |
| Monomer concentration | 0.1 M |
| Electrolyte | 0.3 M NaOH |
| Constant voltage | +0.7 V (VS SCE) |
| Electric charge | 125 mc/cm² |

Figure 4:
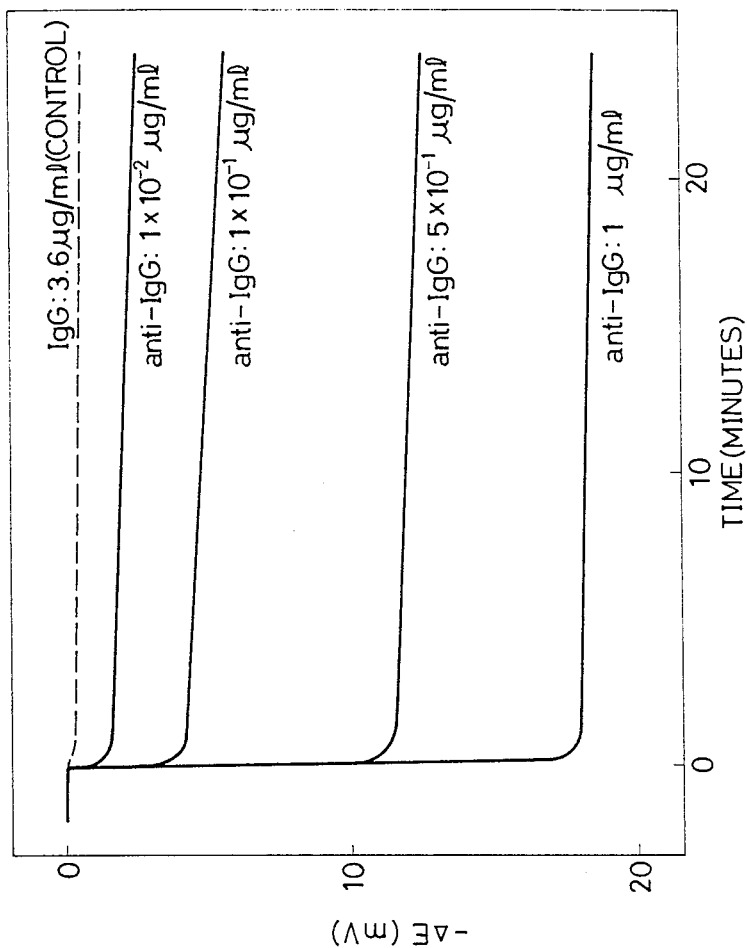
FIG. 4 is a graph showing the response of another embodiment of the present invention.
Figure 5:
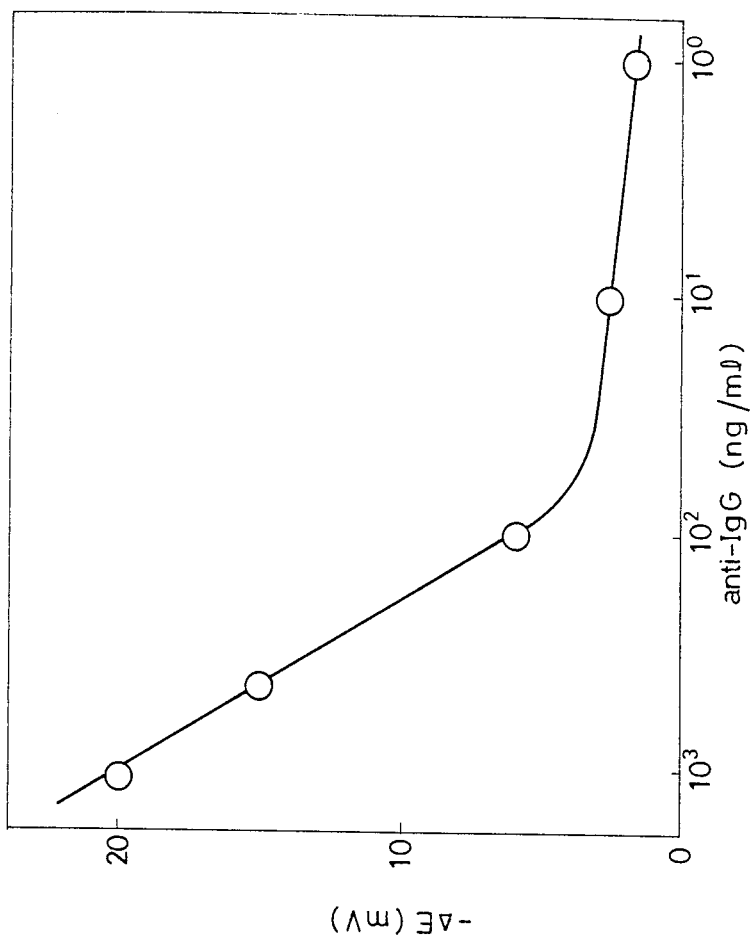
FIG. 5 shows a calibration line based on FIG. 4.

The so-obtained Pt electrode overcoated with polytyramine (thickness of the film: 500–1000 nm) was immersed for three hours at room temperature in 0.1% NaCl solution (pH 4.5 adjusted with HCl) containing 26 mg/ml of carbondiimido and 15.0 mg/ml of IgG under agitation so as to obtain an IgG fixed polytyramine coated electrode. The electrode obtained was immersed, as a working electrode in the immunosensor system as shown in FIG. 1, in a solution containing $\bar{a}$-IgG at various concentrations, and $-\Delta E/mV$ was measured. The results obtained are shown in FIG. 4, which shows that the electrode of the present invention exhibited a good response at any concentration.

Figure 6:
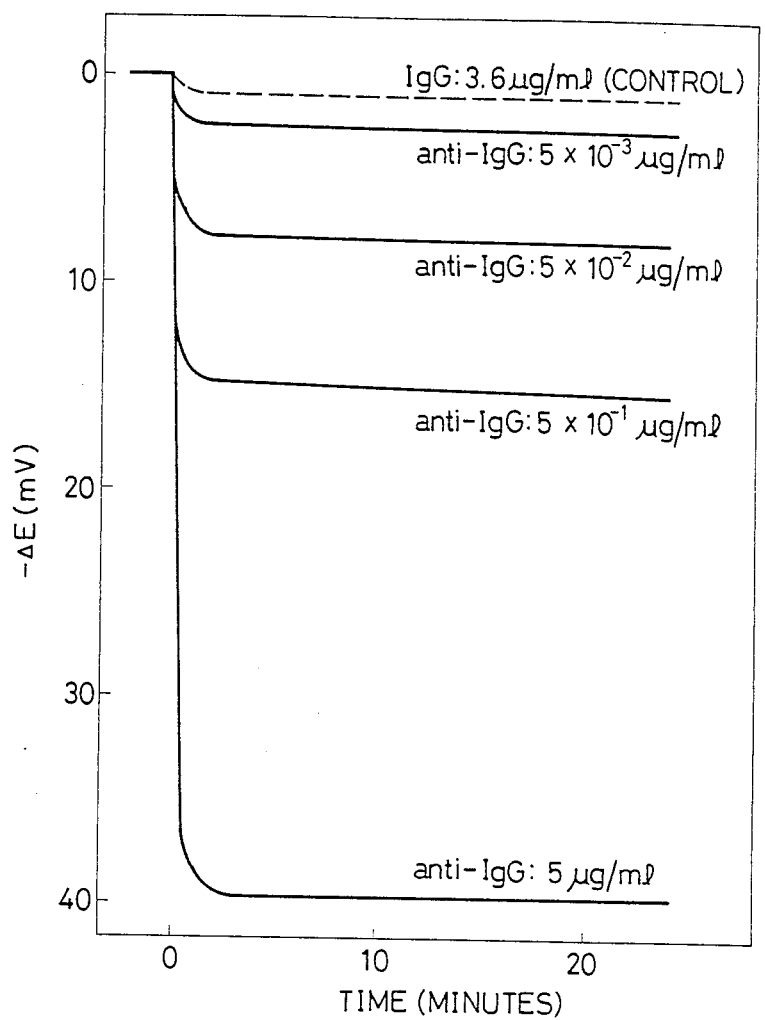
FIG. 6 is a graph showing the response of another embodiment of the present invention.

The calibration line based on the above is shown in FIG. 6.

EXAMPLE 3

An polymerization of 1-(2-cyanoethyl) pyrrol

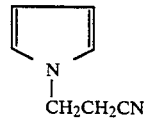

conducted by constant current electrolytic polymerization under the following conditions:

| | |
|---|---|
| Working electrode | 1 mmφ, 5 mm Pt wire |
| Counter electrode | Pt plate |
| Solvent | Acetonitrile |
| Monomer concentration | 0.1 M |
| Electrolyte | 0.1 M[CH₃(CH₂)₃]₄N.BF₄ |
| Current density | 125 μA/cm² |
| Electric charge | 150 mc/cm² |

The 2-cyanoethyl group of the resulting polymer, poly(1-(2-cyanoethyl)pyrrole) was changed to 2-aminoethyl group ($-CH_2CH_2NH_2$) by treating the polymer at a temperature of about 66° C. (boiling point of THF) for 15 minutes with 1M LiAlH₄ in THF. Thereafter, the resulting electrode was immersed in a solution containing IgG at a concentration of 75 mg/ml in the same manner as described in Example 2 so as to obtain an IgG fixed poly[1-(2-aminoethyl)pyrrol)] coated electrode. Response to $\bar{a}$-IgG determined by the same method as described in Example 2 was as shown in FIG. 6, which shows a good response.

From the results as shown above, it is apparent that a potential-causing membrane using electro-conductive polymer having the functional group of the present invention shows a good response as an immunosensor.

What is claimed is:

1. A potential-causing membrane for use in immunosensors, which comprises an electrically-conductive film of polymer being prepared by electrolytic polymerization of electrolytic polymerizable monomer, said polymer having at least one functional group capable of binding an antigen or an antibody per monomer unit thereof in which the functional group is selected from the group consisting of halogen, —CHO, —NH₂ and —COOH, and binding the antigen or the antibody through the functional group thereonto, wherein the monomer unit of said polymer is selected from the group consisting of pyrrole, thiophene, furan, phenol and aniline, and wherein the thickness of the film is between about 0.5μ and about 5 μ.

2. A potential-causing electrode for use in immunosensors, which comprises an electrically-conductive film of polymer being prepared by electrolytic polymerization of electrolytic polymerizable monomer, said polymer having at least one functional group capable of binding an antigen or an an antibody per monomer unit thereof in which the functional group is selected from the group consisting of halogen, —CHO, —NH₂ and —COOH, and binding the antigen or the antibody through the functional group thereonto, wherein the monomer unit of said polymer is selected from the group consisting of pyrrole, thiophene, furan, phenol and aniline, and wherein the thickness of the film is between about 0.05μ and about 0.25μ.

* * * * *